United States Patent [19]
Campbell et al.

[11] Patent Number: 5,067,962
[45] Date of Patent: Nov. 26, 1991

[54] BIOPROSTHETIC LIGAMENT

[75] Inventors: Todd D. Campbell, Corona; Michael A. Zozaya, Laguna Hills, both of Calif.

[73] Assignee: Baxter International Inc., Deerfield, Ill.

[21] Appl. No.: 590,312

[22] Filed: Sep. 28, 1990

Related U.S. Application Data

[63] Continuation of Ser. No. 339,804, Apr. 18, 1989, abandoned.

[51] Int. Cl.$^5$ ............................................... A61F 2/08
[52] U.S. Cl. ........................................................ 623/13
[58] Field of Search ......................... 623/12, 13, 16, 18

[56] References Cited
U.S. PATENT DOCUMENTS

| | | | |
|---|---|---|---|
| 4,400,833 | 8/1983 | Kurland | 623/13 |
| 4,467,478 | 8/1984 | Jurgutis | 623/13 |
| 4,597,766 | 7/1986 | Hilal et al. | 623/13 |
| 4,605,414 | 8/1986 | Czajka | 623/13 |
| 4,668,233 | 5/1987 | Seedhom et al. | 623/13 |
| 4,776,851 | 10/1988 | Bruchman et al. | 623/13 |

OTHER PUBLICATIONS

Smith, Jr. et al., "Bioprosthesis in Hand Surgery", Journal of Surgical Research, 41, 378-387 (1986).
Hinze et al., "Distale Verankerung des freien Beugesehnentransplantats mit eninen Knochenkeil, Zentralblat fur Chirugia 100" (1975) 663-673.

Primary Examiner—David J. Isabella
Attorney, Agent, or Firm—Gordon L. Peterson; June M. Bostich; Michael C. Schiffer

[57] ABSTRACT

A xenograft replacement ligament to replace a damaged anterior cruciate or other human ligament includes a ligament of suitable size and strength that has been harvested from a donor animal with a bone piece at least one end to preserve intact a substantial portion of a first natural ligament-to-bone attachment structure of the donor animal. Once harvested, it may be tanned and otherwise processed with glutaraldehyde solution. Installation includes pinning and otherwise attaching the bone piece at the natural attachment site of the patient to more closely replicate the natural ligament-to-bone attachment structure being replaced. The replacement ligament may be harvested with a bone piece at each end for this purpose, with each of the bone pieces then being attached at a natural attachment site of each of two bones of the patient.

5 Claims, 1 Drawing Sheet

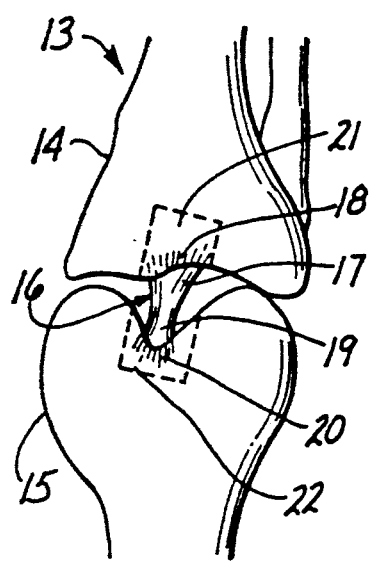
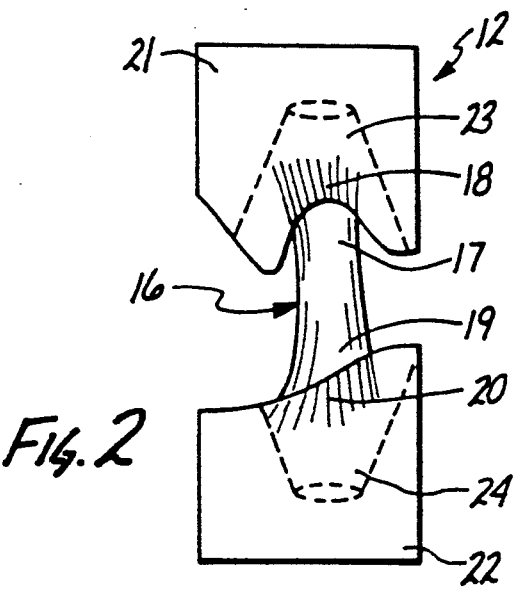
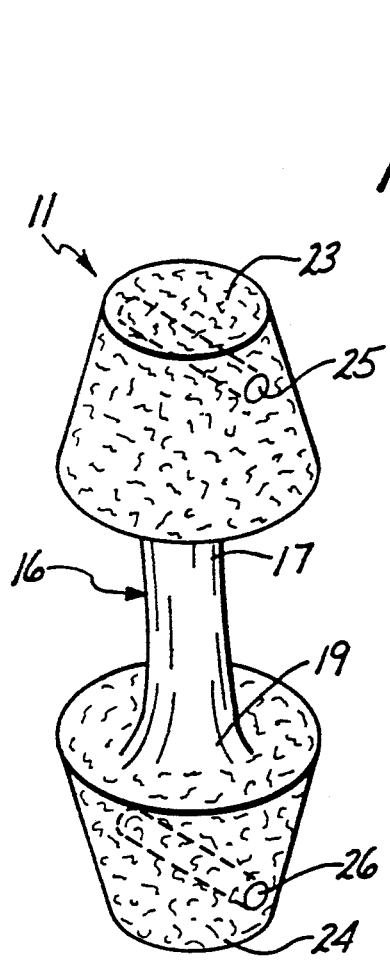
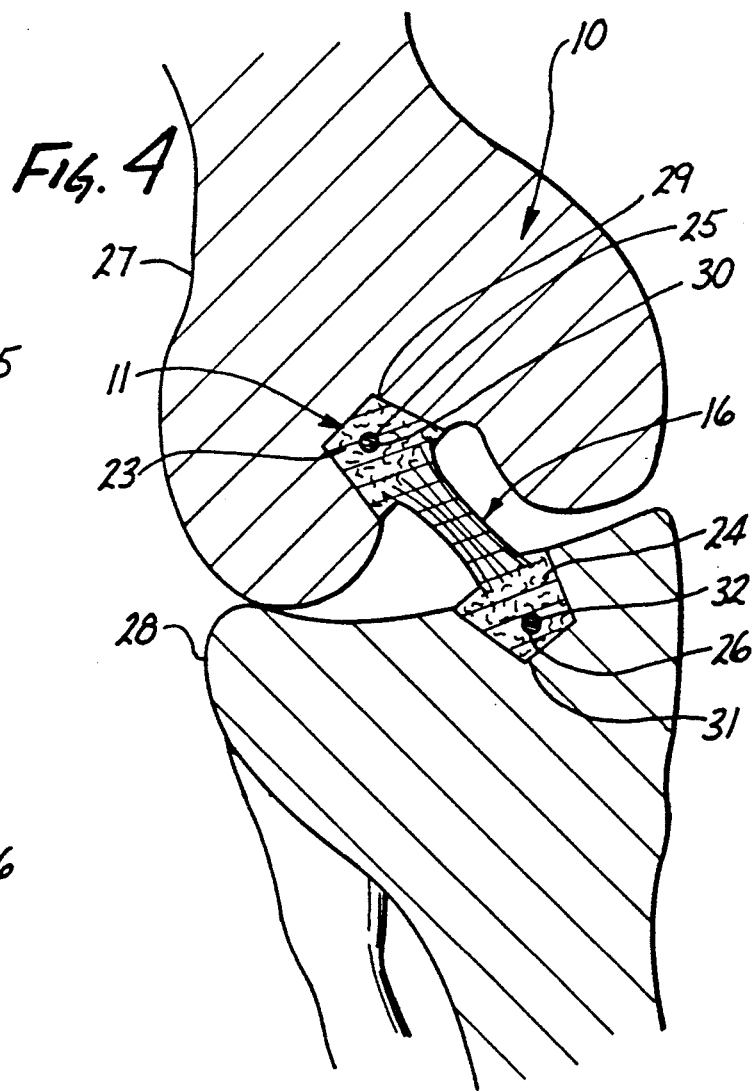

5,067,962

BIOPROSTHETIC LIGAMENT

This is a continuation of application Ser. No. 07/339,804, filed on Apr. 18, 1989, now abandoned.

BACKGROUND OF THE INVENTION

1. Technical Field

This invention relates generally to prosthetics, and more particularly to a new and improved replacement ligament.

2. Background Information

Replacement ligaments can restore performance where native structures rupture beyond repair. But success depends on proper attachment to the host bone. Thus, the manner in which this is done and the related details of prosthesis construction are important.

Consider, for example, an injured knee joint having a damaged anterior cruciate ligament. Attachment of a replacement ligament according to existing techniques may involve forming tunnels in the femur and tibia (the host bones). The tunnels are formed so that each extends through one of the host bones from an entrance or proximal end of the tunnel at the natural ligament attachment site to an exit or distal end of the tunnel at an outer surface of the host bone.

Each end of the replacement ligament is passed through one of the tunnels, from the proximal end to the distal end where it is anchored to the outer surface of the host bone by such means as stapling. This results in the replacement ligament spanning the intra-articular region between the natural attachment sites somewhat like a natural ligament, but it also results in certain problems that need to be overcome.

For example, the replacement ligament extends beyond the natural attachment sites and all the way through the tunnels to the outer surfaces on the other side of each host bone. This results in the replacement ligament being able to stretch over a greater length than a natural ligament (from the outer surface of the femur to the outer surface of the tibia), and this impairs performance.

In addition, formations such as bone spicules can form at the entrance to each of the tunnels. These tend to abrade the replacement ligament, cause fatigue of the material, and break off particles which can cause irritation.

Furthermore, the tunnels provide access to the host bone interior. As a result, synovial fluid can migrate from the intra-articular region between host bones into the bone tunnels. Thus, any activity in the intra-articular region, such as infection, can be easily communicated into the bone interior and result in intra-osseous complications. Similarly, activity within the bone can be easily communicated to the intra-articular region.

Consequently, it is desirable to have a new and improved replacement ligament and attachment method that overcomes these concerns.

SUMMARY OF THE INVENTION

This invention solves the problems outlined above with a xenograft, glutaraldehyde-preserved, replacement ligament that is harvested to retain a piece of donor bone in order to keep the donor's natural attachment site intact. Implantation of the bone piece at the recipient's natural attachment site results in a bioprosthetic ligament that has a natural ligament-to-bone attachment located at the natural attachment site, and this overcomes many problems of existing ligament prostheses.

Generally, a method of attaching a replacement ligament according to a major aspect of the invention includes providing a ligament of suitable size and strength that has been harvested from a donor animal. The ligament has first and second end portions, and it is harvested so that at least a first bone piece remains attached to the first end portion in order to preserve intact a substantial portion of a first natural ligament-to-bone attachment structure of the donor animal at the first end portion.

The first bone piece is attached to a first bone of the patient at the natural attachment site on the first bone and the second end portion of the ligament is attached to a second bone of the patient.

The ligament may be harvested with a bone piece at each end. In addition, it may be tanned and processed with a glutaraldehyde solution, the bone pieces may be implanted in recesses formed in the bones of the patient at the natural attachment sites, and the bone pieces may be pinned in place. In these ways, the surgeon can more closely replicate the natural attachment structures being replaced.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 of the drawings is a diagrammatic representation of a bovine joint showing a ligament to be harvested;

FIG. 2 is an enlarged view of the ligament to be harvested showing the cuts made in dashed lines that preserve the natural attachment sites;

FIG. 3 is a perspective view of a replacement ligament that has been manufactured from the harvested ligament; and FIG. 4 is a diagrammatic view of the replacement ligament installed between a human tibia and femur as a replacement for the anterior cruciate ligament.

DESCRIPTION OF THE PREFERRED EMBODIMENTS

Referring now to the drawings, there is shown a replacement ligament installation 10 constructed according to the invention (FIG. 4) that replaces a human anterior cruciate ligament utilizing a bioprosthetic or replacement ligament 11 (FIG. 3) which has been manufactured from a harvested ligament 12 (FIG. 2) taken from a joint of a donor animal such as from a bovine joint 13 (FIG. 1). Of course, the inventive concepts disclosed apply to replacement ligaments manufactured from harvested ligaments that are taken from sources other than a bovine joint (porcine and other large animals, for example) and to replacement uses other than as a replacement anterior cruciate ligament.

The bovine joint 13 includes a first bone 14, a second bone 15, and a bovine ligament 16, the bovine ligament 16 being chosen so that its size and strength are sufficient for human weight bearing application, and it is removed in such a manner to leave intact the naturally occurring ligament-to-bone attachment. A first end portion 17 of the bovine ligament 16 (FIG. 1) is attached to the first bone 14 at a first naturally occurring ligament-to-bone attachment site (an attachment site 18) and a second end portion 19 of the bovine ligament 16 is attached to the second bone 15 at a second naturally occurring ligament-to-bone attachment site (an attachment site 20).

To remove the bovine ligament 16 so that first and second bone pieces 21 and 22 remain attached, it may be necessary to remove the knee capsule and menisci and carefully cut the bone structure away until the attachment sites 18 and 20 are visible. Then, the bone pieces 21 and 22 are cut from the first and second bones 14 and 15 along the regions indicated in dashed lines in FIG. 1 to preserve the attachment sites 18 and 20 intact. Doing this results in the harvested ligament 12 illustrated in FIG. 2.

Once harvested, the harvested ligament 12 is rinsed and machined to form first and second bone plugs 23 and 24 indicated by the dashed lines in FIG. 2. The bone plugs 23 and 24 are utilized in the replacement ligament installation 10, and they are dimensioned and arranged to fit within recesses formed in the human bones to which they will be attached as subsequently described.

Any conventional means of machining hard materials may be used to obtain the desired final shape of the bone plugs 23 and 24, including the use of drills, lathes, saws, and other tools. Doing this results in the replacement ligament 11 illustrated in FIG. 3.

First and second holes 25 and 26 may be machined in the first and second bone plugs 23 and 24 for use in anchoring the bone plugs 23 and 24 in place, such as by pinning as subsequently described, the bone plugs 23 and 24 may then be cleaned to remove machine oils and debris and also to surface defat the material. Any suitable solvent can be used for this purpose, a preferred procedure including submersion of the bone in 100% ethanol followed by saline rinses.

The replacement ligament 11 may then be chemically processed. Advantageously, the bone piece is next treated to increase the porosity of the matrix and thus to further encourage ingrowth of host bone into the grafting material. This treatment may be accomplished by extracting the bone with an organic solvent, such as chloroform, 100% ethanol, cholorform:methanol (1:1), acetone, or similar solvents, followed by rinsing in physiological saline to remove the organic solvent. Optionally, this porosity-increasing step may include treatment of the bone piece with a protease such as that sold under the trademark Pronase, collagenase or hyaluronidase.

In a particular preferred procedure, the bone plugs 23 and 24 are submerged in a buffered Pronase solution at thirty-seven degrees Centigrade for twenty-four hours, followed by rinsing in buffered normal saline and extraction with cholorform:methanol (1:1) by submersion for one hour with constant stirring at twenty-five degrees Centigrade, followed by rinsing in buffered normal saline.

This treatment removes nonmatrix-bound (non-collagenous) proteins. Desirably, all such proteins are removed. If all such proteins are removed, the porosity of the matrix can be increased by as much as ten percent. The treatment also further reduces the antigenicity of the material. The level of porosity can be determined by visual inspection and confirmed by light or electron microscopy.

The bone plugs 23 and 24 are stored in a 0.625% HEPES-buffered glutaraldehyde. After inspection, the replacement ligament 11 is sterilized, rinsed, and packaged in 0.05% HEPES-buffered glutaraldehyde. The glutaraldehyde treatment imparts many desirable properties to the material. For example, cross-linking of proteins by glutaraldehyde renders the material non-antigenic so that it may be implanted in a host other than the one from which the stock bone was taken to produce the grafting material.

Glutaraldehyde-treated bone has been found to have excellent biocompatibility. When glutaraldehyde-treated bone is implanted in mammalian host bone, there is generally no fibrous encapsulation, interposition or fibrous tissue between host bone and implanted bone, or other evidence of rejection.

Following glutaraldehyde tanning, the bone plugs 23 and 24 may be further sterilized by any suitable means, including radiation or immersion in ethanol or bacteriocidal solution. Preferably, a buffered surfactant/formaldehyde ethanol sterilant is used. The grafting material may be stored in a suitable sterile solution such as 0.05% (w/v) glutaraldehyde in HEPES buffer, in sterile containers until needed.

Of course, various changes may be incorporated in the above fabrication procedure and the bone plugs 23 and 24 can be otherwise shaped and dimensioned depending on the precise application.

Installation of the replacement ligament 11 as an anterior cruciate ligament between a femur 27 and a tibia 28 results in the replacement ligament installation 10 illustrated in FIG. 4. The bone plug 23 is implanted or placed within a first recess 29 formed by suitable known means in the femur 27 at the naturally occurring attachment site on the femur 27 of the ligament being replaced. There, it is attached or anchored to the femur 27 by suitable means such as a first stainless steel pin 30 through the hole 25. Similarly, the bone plug 24 is placed within a second recess 31 formed in the tibia 28 at the naturally occurring attachment site on the tibia 28. There, it is attached or anchored to the tibia 28 by suitable means such as a second stainless steel pin 32 through the hole 26.

Thus, this invention solves the problems outlined above with a xenograft, glutaraldehyde-preserved, replacement ligament that is harvested to retain a piece of donor bone in order to keep the donor's natural attachment site intact. In that regard, the words "at the natural attachment site" in such claim language as "attaching the first bone piece to a first bone of the patient at the natural attachment site on the first bone" and "forming a recess in the first bone of the patient at the natural attachment site on the first bone" means at least closely adjacent to the natural attachment site.

Although an exemplary embodiment of the invention has been shown and described, many changes, modifications, and substitutions may be made by one having ordinary skill in the art without necessarily departing from the spirit and scope of the invention.

What is claimed is:

1. A method of replacing a damaged or diseased ligament with a replacement preserved animal ligament having first and second end portions connected to a piece of that ligament natural bone, which bone piece is shaped into a plug comprising;
   securing the first ligament end bone piece into a recess formed in that bone of the patient to which an end of the damaged or diseased ligament is attached; and
   securing the second ligament end bone piece into a recess formed in that bone of the patient to which a second end of the damaged or diseased ligament is attached.

2. A method as recited in claim 1, wherein the steps of securing include:
   forming the recess in each of the patient's bones at the natural damaged or diseased ligament attachment site; and
   implanting the first and second ligament end bone piece in the recess.

3. A method as recited in claim 2, wherein the steps of securing include:
   shaping the bone pieces into a first bone plug dimensioned and arranged to fit within the recesses in the bone.

4. A method as recited in claim 2 further including the step of:
   mechanically fixing each of the ligament end bone pieces in each of the recesses.

5. A method as recited in claim 4 wherein the step of mechanically fixing includes:
   placing a pin through each of the ligament end bone pieces and the patient's bone.

* * * * *